United States Patent [19]

Nobles

[11] Patent Number: 5,207,684
[45] Date of Patent: May 4, 1993

[54] SHEATH FOR SHUNT PLACEMENT FOR HYDROCEPHALUS

[75] Inventor: Anthony A. Nobles, Fountain Valley, Calif.

[73] Assignee: Neuro Navigational Corporation, Costa Mesa, Calif.

[21] Appl. No.: 867,826

[22] Filed: Apr. 13, 1992

[51] Int. Cl.⁵ .................. A61M 25/00; A61B 17/00
[52] U.S. Cl. .................. 606/108; 606/27; 606/29; 606/32; 606/37; 606/39; 606/40; 606/45; 606/167
[58] Field of Search .................. 604/8–10, 604/22, 27, 93; 606/28, 29, 27, 37, 39, 32, 40, 45–50, 108, 170, 167

[56] References Cited

U.S. PATENT DOCUMENTS

| | | | |
|---|---|---|---|
| 3,020,913 | 2/1962 | Heyer | 604/9 |
| 4,562,838 | 1/1986 | Walker | 606/49 |
| 4,682,596 | 7/1987 | Bales et al. | 606/39 |
| 5,057,107 | 10/1991 | Parins et al. | 606/48 |
| 5,084,045 | 1/1992 | Helenowski | 606/48 |

Primary Examiner—Stephen C. Pellegrino
Assistant Examiner—Glenn Dawson
Attorney, Agent, or Firm—John L. Rogitz

[57] ABSTRACT

A sheath through which a shunt for relieving hydrocephalus can be withdrawn from or advanced into the brain of a patient includes a tubular member which is slidably engageable with the shunt in a surrounding relationship with the shunt. The tubular member has a distal end segment, and an electrically resistive cutting element is positioned on the distal end segment for selectively cutting tissue adjacent the cutting element as the tubular member is advanced over the shunt. Preferably, the cutting element is connected to a source of electrical pulses for selectively heating the cutting element and thus for selectively thermally cutting tissue that has grown into the shunt away from the shunt. The sheath also includes a small fiber tube through which an optical fiber can be positioned to provide a means for presenting a video display of the brain during shunt retrieval and replacement through the sheath.

17 Claims, 2 Drawing Sheets 5,207,684

SHEATH FOR SHUNT PLACEMENT FOR HYDROCEPHALUS

FIELD OF THE INVENTION

The present invention relates generally to surgical instruments, and more particularly to neurosurgery tools.

BACKGROUND

Hydrocephalus, familiarly known as water on the brain, is an affliction which affects many people, including children. One of the symptoms of this serious malady is increased fluid pressure on the brain of the victim, which, unless relieved, can result in excruciating pain, and can potentially cause brain damage to the victim.

Hydrocephalus causes a slow, continuous build-up of fluid pressure on the brain. More specifically, in a patient afflicted with hydrocephalus, excess body fluid slowly and continuously accumulates between the ventricles of the brain. To extract the excess body fluid from between the ventricles of the brain and thereby relieve the fluid pressure on the brain, techniques have been developed for establishing a pathway for fluid communication from the area of accumulated fluid to an area external to the cranial cavity.

As an example of one such well-known technique, a long, slender catheter known as a "shunt" is advanced through a small entry site in the neck of a patient who is afflicted with hydrocephalus, and a distal end segment of the shunt is positioned between the ventricles of the brain. The end of the shunt that is opposite to the distal end segment is positioned in the chest cavity of the patient. Typically, a plurality of small holes are formed in the distal end segment of the shunt, and fluid that accumulates in the brain enters the holes and drains through the shunt into the chest cavity of the patient, thereby relieving the fluid pressure on the brain.

Unfortunately, the small holes in the distal end segment of the shunt can become clogged, thereby impeding the draining of excess fluid from the cranial cavity. More specifically, a portion of the brain known as the choroid plexus can grow into the holes of the distal end segment of the shunt and clog the holes. When this occurs, it is necessary to remove the shunt from the brain and replace the shunt with another unclogged shunt.

The clogged shunt, however, cannot simply be pulled out of the brain, with portions of the choroid plexus still attached to it, without risking damage to the brain. Thus, when a shunt becomes clogged, it is necessary to perform a relatively invasive surgical procedure to gain access to the distal end segment of the shunt and gently cut away the ingrown portions of the choroid plexus. Not surprisingly, it is desireable to avoid performing invasive procedures on the brain, to avoid undue risk of brain damage and infection, and to reduce overall patient discomfort.

Accordingly, it is an object of the present invention to provide a device for separating ingrown portions of the brain from a shunt that has been positioned in the brain to relieve hydrocephalus. It is another object of the present invention to provide a device for separating ingrown portions of the brain from a shunt without recourse to relatively invasive surgery. It is a further object of the present invention to provide a device for separating ingrown portions of the brain from a shunt which is easy to use and cost-effective to manufacture.

SUMMARY

A device for withdrawing a shunt from the brain of a patient includes a tubular member that is slidably engageable with the shunt in a surrounding relationship therewith. The tubular member has a distal end segment, and a cutting element is positioned on the distal end segment for selectively cutting tissue which is adjacent to the cutting element as the tubular member is advanced over the shunt.

In a preferred embodiment, the cutting element is electrically resistive, and a source of electricity is electrically connected to the cutting element for selectively energizing the cutting element to cut tissue. The cutting element can advantageously be made of metal or ceramic.

In one embodiment, the cutting element is cylindrically-shaped, to establish an electrical monopole cutting element. In another embodiment, the cutting element has first and second collars that conform to the shape of the tubular member and that are spaced apart from each other, to establish an electrical dipole cutting element. In the electrical dipole embodiment, each collar has first and second co-parallel straight edges, and the collars are positioned on the tubular member with the first edge of one collar closely spaced from the first edge of the other collar and the second edge of one collar closely spaced from the second edge of the other collar. In either embodiment, the tubular member can have a first lumen for engaging the shunt and a second lumen for establishing a passageway for an optical fiber.

In another aspect of the present invention, a sheath for selectively cutting tissue away from a shunt having a distal end segment that has been positioned in a patient's brain for relieving hydrocephalus in a patient's brain includes a tubular member. The tubular member is slidably engageable with the shunt in a surrounding relationship therewith for advancing the tubular member over the shunt into the patient's brain. In accordance with the present invention, the tubular member has a distal end segment configured for cutting tissue adjacent the distal end segment of the tubular member away from the distal end segment of the shunt.

In yet another aspect of the present invention, a method is disclosed for extracting a shunt from the brain of a patient. In accordance with the method of the present invention, a tubular member is provided which has a distal end segment and a cutting element operably engaged with distal end segment. The tubular member is slidably engaged with the shunt and advanced over the shunt into the patient's brain. As the tubular member is advanced into the patient's brain, the cutting element is activated to cut tissue away from the shunt. To provide a visual image of the brain to the surgeon, a fiber optic that is connected to a video display system can be advanced through the tubular member for generating a video image of the patient's brain.

These and other features of the present invention can best be understood in reference to the accompanying drawings, in which like reference numerals refer to like parts, and in which:

DESCRIPTION OF THE PREFERRED EMBODIMENT

Figure 1:
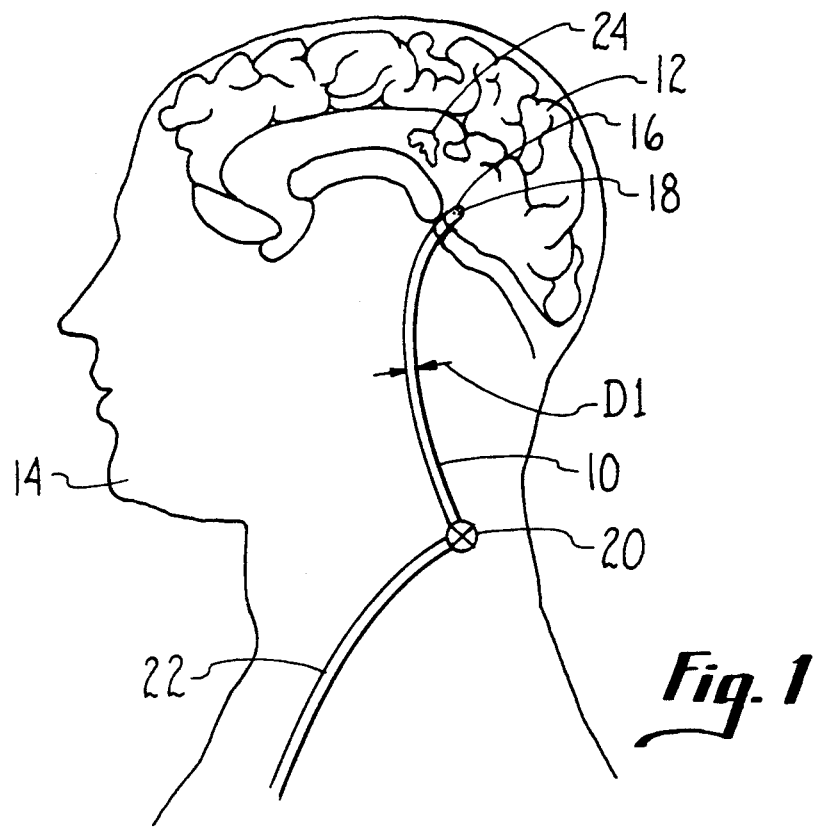
FIG. 1 is a perspective view of a shunt that has been positioned in a patient for relieving fluid pressure on the patient's brain.

Referring initially to FIG. 1, a shunt 10, of the type known in the art for relieving hydrocephalus in a patient, has been positioned between the ventricles of a brain 12 of a patient 14, to relieve fluid pressure on the brain 12. The shunt 10 is essentially a hollow tube that has a closed distal end segment 16 which is formed with a plurality of holes 18. Typically, the shunt 10 has an outer diameter D1 of about three millimeters (3mm) Excess fluid in the cranial cavity flows through the holes 18 into the shunt 10 and through a valve 20, which is positioned in the neck of the patient 14.

The valve 20 can be adjusted prior to implantation in the patient 14 to establish a predetermined flow rate through the valve 0. In one presently preferred embodiment, the valve 20 is a "Ventricular Shunt Valve" made by PS Medical of Goleta, California.

A drain tube 22 is connected to the valve 20 to establish a passageway for fluid communication from the valve 20 into the chest cavity of the patient 14. Thus, excess fluid from the cranial cavity of the patient 14 can enter the holes 18 of the shunt 10 and drain into the chest cavity of the patient 14 through the drain tube 22 to thereby relieve fluid pressure on the brain of the patient 14.

The above-described apparatus is effective for relieving the symptoms of hydrocephalus in the patient 14, unless the holes 18 of the shunt 10 become clogged. Such an event can occur when the distal end segment 16 of the shunt 10 is inadvertently positioned near the choroid plexus 24, which is a portion of the brain 12 of the patient 14 that can grow into the holes 18. When the holes 18 become clogged by ingrown portions of the choroid plexus, as shown in FIG. 2, the effectiveness of the shunt 10 in relieving hydrocephalus is diminished.

A clogged shunt 10 must accordingly be removed from the patient 14 and replaced with another shunt (not shown). A clogged shunt 10 cannot easily be removed from the patient 14, however, without risking damage to the brain 12 of the patient 14, because the ingrown portions of the choroid plexus tend to tear away portions of the brain 12 when the shunt 10 is retrieved from the brain 12 of the patient 14. Consequently, relatively invasive surgery may be required to gently cut away the ingrown portions of the choroid plexus 24, prior to removing a clogged shunt 10 from a patient 14.

Figure 2:
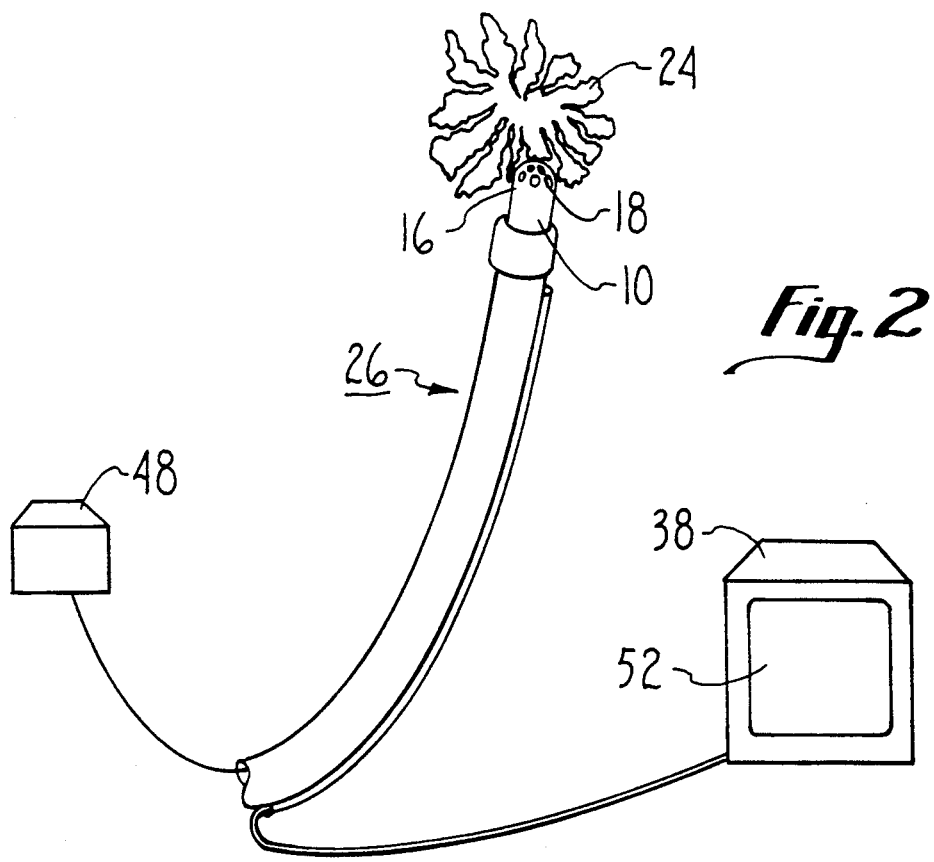
FIG. 2 is a perspective view of the novel sheath for shunt placement for hydrocephalus of the present invention, shown being advanced over a shunt into a patient's brain, showing the choroid plexus of the brain.

FIG. 2 shows that the present invention recognizes that a clogged shunt 10 can be efficaciously removed from the brain 12 without undue risk of harm to the patient 14, and without requiring relatively invasive surgery. More specifically, a sheath, generally designated 26, can be advanced over the shunt 10 to cut tissue (e.g., the choroid plexus 24) away from the shunt 10 to facilitate withdrawal of the shunt 10 from the brain 12 of the patient 14, as more fully disclosed below.

Figure 3:
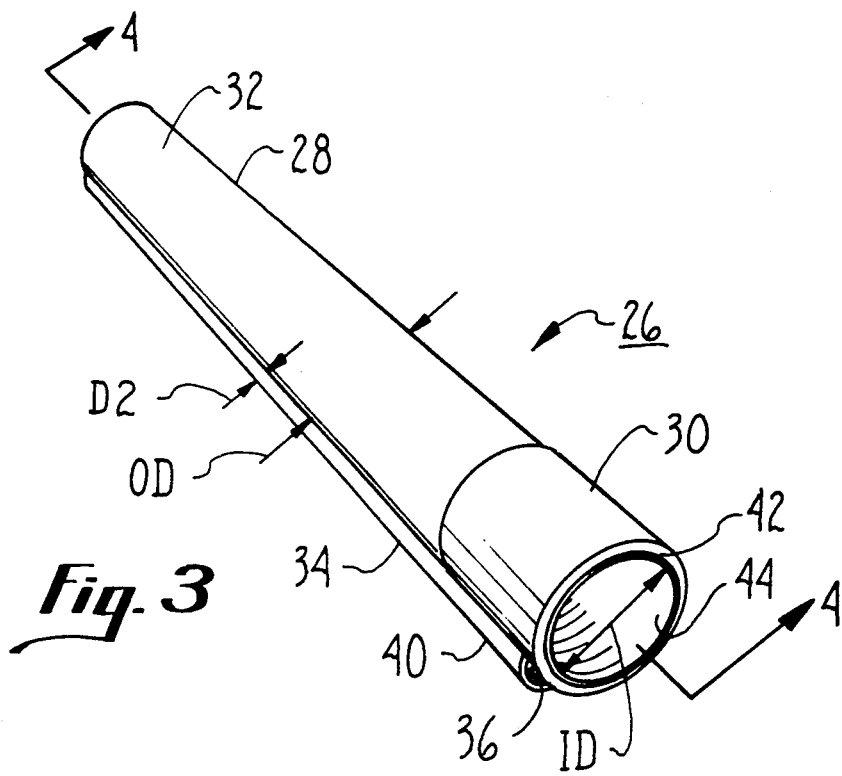
FIG. 3 is a perspective view of the novel sheath for shunt placement for hydrocephalus of the present invention.
Figure 4:
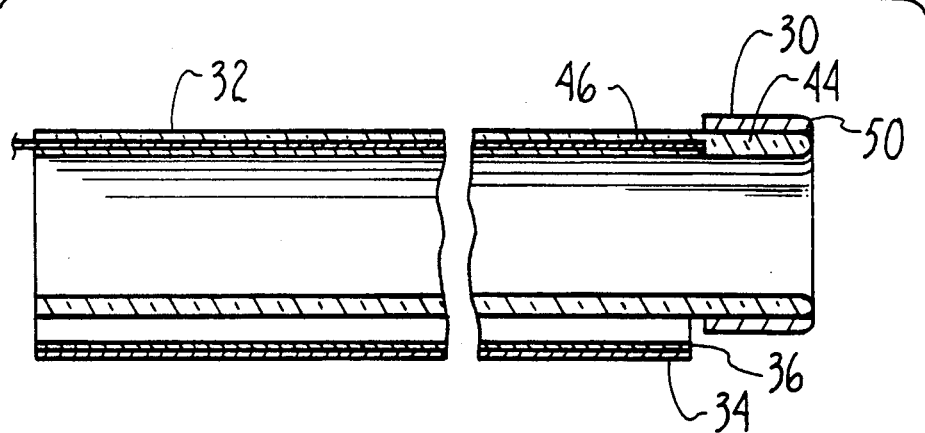
FIG. 4 is a cross-sectional view as seen along the line 4—4 in FIG. 3.

Referring now to FIGS. 3 and 4, the details of the sheath 26 can be seen. As shown in FIG. 3, the sheath 26 includes a tubular member 28, preferably made of a disposable material, such as plastic, and a cutting element 30. The tubular member 28 includes a hollow, flexible, thin-walled catheter-like main tube 32 that has an inside diameter ID of between about one and one-half millimeters to about nine millimeters (1.5mm-9mm) and an outer diameter OD which is marginally greater than the inside diameter ID. The skilled artisan will appreciate that the precise dimensions of the tube 32 will be established to provide a close slidable fit with the shunt 10. Thus, the main tube 32 of the tubular member 28 can be slidably engaged with the shunt 10 in a close surrounding relationship therewith. It will be appreciated that placement of the tubular member 28 into the patient 14 only marginally increases the required diameter of the entry site into the patient 14 which must be made incident to placement of the shunt 10 inside the brain 12 of the patient 14. In one presently preferred embodiment, as stated above, the tubular member 28 is made of a flexible, axially rigid, biocompatible catheter material, such as wire-reinforced plastic tubing.

FIG. 3 shows that the tubular member 28 also includes a fiber optic tube 34 that is attached to or formed integrally with the main tube 32. The fiber optic tube 34 has a diameter D2 of about one-quarter to four millimeters (0.25mm-4.0mm). Thus, the tubular member 28 essentially has two lumens—a first one established by the main tube 32, and a second one established by the fiber optic tube 34. At least one optical fiber 36 is positioned in the fiber optic tube 34 to illuminate the brain 12 of the patient 14 and to conduct back to a video display system 38 (FIG. 2) an image of the brain 12. As shown, the distal end 40 of the fiber optic tube 34 does not extend completely the length of the main tube 32, but instead is positioned proximally relative to the distal end 42 of the main tube 32.

Still referring to FIGS. 3 and 4, the cutting element 30 is shown to be a hollow, annular, cylindrically-shaped member that is positioned on the distal end segment 44 of the main tube 32. More specifically, the cutting element 30 is positioned in a surrounding stationary relationship with the outer wall of the main tube 32. Preferably, the cutting element 30 is bonded to the main tube 32 by solvent bonding or potting the cutting element 30 to the main tube 32.

In the presently preferred embodiment, the cutting element 30 is made of a biocompatible electrically resistive material, such as a ceramic or a metal (e.g., copper, stainless steel). As best shown in FIG. 4, an electrical lead 46 is potted in the wall of the main tube 32 and is electrically connected to the cutting element 30. The lead 46 extends through the main tube 32 and is electrically connected to a source 48 of electricity (FIG. 2). In one presently preferred embodiment, the source 48 is a Bovie model electrical generator which produces pulses of electricity in response to manipulation of the Bovie by the operator of the sheath 26. Thus, pulses of electricity can be applied to the cutting element 30 to selectively heat the element 30 and thereby selectively thermally cut or cauterize tissue which is adjacent the cutting element 30.

FIG. 4 shows that the distal edge 50 of the cutting element 30 may be slightly rounded, in order to avoid mechanically damaging tissue of the patient 14 when the sheath 26 is advanced into the brain 12 of the patient 14.

In the operation of the sheath 26, reference is made to FIGS. 2 and 3. When it has been determined that the shunt 10 has become clogged and thus requires replacement, an entry site is made in the neck of the patient 14, and the shunt 10 is disconnected from the valve 20. The main tube 32 of the sheath 26 is engaged with the shunt 10 and is slid distally into the patient 14, over the shunt 10.

An image of the brain 12 is conducted back through the optical fiber 36 to the video display system 38, which presents a display of the brain 12 on an associated monitor 52 by means well-known in the art. By viewing the display on the monitor 52, the surgeon can determine when the cutting element 30 has been advanced adjacent portions of the choroid plexus 24 that have gron into the holes 18 of the shunt 10. When the cutting element 30 is near ingrown portions of the choroid plexus 24, the surgeon activates the source 48 of electricity to heat the cutting element 30 and thereby thermally cut away the ingrown portions from the shunt 10.

After the choroid plexus 24 has been separated from the shunt 10, the shunt 10 may be withdrawn from the patient 14 through the sheath 26. Then, a new shunt (not shown) is advanced through the sheath 26, and the distal end segment of the new shunt positioned in the brain 12 of the patient 14. When placing the new shunt into the brain 12, the surgeon can view the video monitor 52 to avoid placing the distal end segment near the choroid plexus 24. The sheath 26 is then removed from the patient 14, and the new shunt connected to the valve 20 to reestablish a fluid passageway from the brain 12 to the chest cavity of the patient 14.

Figure 5:
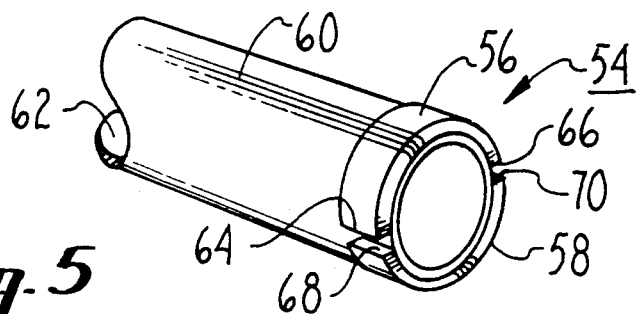
FIG. 5 is a perspective view of an alternate embodiment of the novel sheath of the present invention.

It will be appreciated in reference to the above disclosure that the cutting element 30 establishes an electrical monopole. FIG. 5 shows a cutting element, generally designated 54, which establishes an electrical dipole (sometimes familiarly referred to as a bipolar cutting element). More particularly, the cutting element 30 has first and second collars 56, 58 which are not connected to each other (i.e., which are closely spaced apart from each other).

As shown, the collars 56, 58 conform to a tubular member 60 of a sheath 62. The first collar 56 has first and second co-parallel straight edges 64, 66, while the second collar 58 has first and second co-parallel straight edges 68, 70. As further shown in FIG. 5, the collars 56, 58 are positioned on the tubular member 60 with the first edge 64 of the first collar 56 closely spaced from the first edge 68 of the second collar 58. Further, the second edge 66 of the first collar 56 is closely spaced from the second edge 70 of the second collar 58. It can be appreciated in reference to FIG. 5 that the collars 56, 58 have arcuate cross-sections. As the skilled artisan will appreciate, when the cutting element 54 is energized with electricity, most of the thermal cutting energy is located between the edges 64, 66, 68, 70 of the collars 56, 58.

While the particular sheath for shunt placement for hydrocephalus as herein shown and described in detail is fully capable of attaining the above-stated objects, it is to be understood that it but a presently preferred embodiment of the present invention, and that the scope of the present invention is accordingly to be limited by nothing other than the appended claims.

I claim:

1. A device, comprising:
   a shunt for relieving hydrocephalus in the brain of a patient;
   a tubular member slidably engageable with the shunt in a surrounding relationship therewith, the tubular member having a distal end segment; and
   a cutting element positioned on the distal end segment for selectively cutting tissue adjacent the cutting element as the tubular member is advanced over the shunt.

2. The device of claim 1, wherein the cutting element is electrically resistive, and is electrically connected to a source of electricity for selectively energizing the cutting element to cut tissue adjacent the cutting element.

3. The device of claim 2, wherein the cutting element is made of metal.

4. The device of claim 3, wherein the cutting element is made of ceramic.

5. The device of claim 2, wherein the cutting element is cylindrically-shaped.

6. The device of claim 2, wherein the cutting element has first and second collars spaced apart from each other.

7. The device of claim 6, wherein each collar conforms to the tubular member, each collar having first and second co-parallel straight edges, the collars being positioned on the tubular member with the first edge of one collar closely spaced from the first edge of the other collar and the second edge of one collar closely spaced from the second edge of the other collar.

8. The device of claim 1, wherein the tubular member has a first lumen for engaging the shunt and a second lumen for establishing a fiber optic passageway.

9. A device for selectively cutting brain tissue, comprising:
   a shunt having a distal end segment that has been positioned in a patient's brain for relieving hydrocephalus in a patient's brain;
   a tubular member slidably engaged with the shunt in a surrounding relationship therewith for advancing the tubular member over the shunt into the patient's brain, the tubular member having a distal end segment configured for cutting tissue adjacent the distal end segment of the tubular member away from the distal end segment of the shunt.

10. The device of claim 9, wherein the distal end segment of the tubular member is configured for selectively thermally cutting tissue.

11. The device of claim 10, wherein the distal end segment of the tubular member includes an electrically resistive cutting element.

12. The device of claim 11, wherein the cutting element is cylindrically-shaped.

13. The device of claim 12, wherein the cutting element comprises first and second collars spaced apart from each other.

14. The device of claim 9, wherein the tubular member has a first lumen for engaging the shunt and a second lumen for establishing a fiber optic passageway.

15. A method for extracting a shunt from the brain of a patient, comprising the steps of:
   (a) providing a tubular member having a distal end segment and a cutting element operably engaged with the distal end segment;
   (b) slidably engaging the tubular member with the shunt;
   (c) advancing the tubular member over the shunt into the patient's brain; and (d) activating the cutting element to cut tissue away from the shunt.

16. The method of claim 15, wherein the cutting element is electrically resistive, and the activating step is accomplished by conducting an electrical pulse to the cutting element.

17. The method of claim 15, further comprising the step of advancing a fiber optic through the tubular member for generating a video image of the patient's brain.

* * * * *